(12) United States Patent
Beebe et al.

(10) Patent No.: US 8,189,872 B2
(45) Date of Patent: May 29, 2012

(54) METHOD FOR QUANTIFYING CELL MOTILITY AND CELL MIGRATION

(75) Inventors: David J. Beebe, Monona, WI (US); Ivar Meyvantsson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1234 days.

(21) Appl. No.: 11/870,740

(22) Filed: Oct. 11, 2007

(65) Prior Publication Data

US 2009/0098597 A1 Apr. 16, 2009

(51) Int. Cl.
 *G06K 9/00* (2006.01)
(52) U.S. Cl. ........ 382/107; 382/100; 382/128; 382/133; 422/50; 435/4; 435/29; 435/283.1; 435/287.1
(58) Field of Classification Search .................. None
See application file for complete search history.

(56) References Cited

U.S. PATENT DOCUMENTS

| | | | |
|---|---|---|---|
| 6,944,316 B2 * | 9/2005 | Glukhovsky et al. | 382/107 |
| 2003/0040031 A1 * | 2/2003 | Kim et al. | 435/29 |
| 2006/0127881 A1 * | 6/2006 | Wong et al. | 435/4 |
| 2008/0131323 A1 * | 6/2008 | Kuczenski et al. | 422/82.13 |

OTHER PUBLICATIONS

Shur et al. Microfabrication Methods for the Study of Chemotaxis, Jun. 2004, MIT.*
*Tools for Anti-Inflammatory Drug Design: In Vitro Models of Leukocyte Migration* by Emma K. Frow et al., Medical Research Reviews, vol. 24, No. 3, 267-298, 2004.
*Neutrophil Chemotaxis in Linear and Complex Gradients of Interleukin-8 Formed in a Microfabricated Device* by Noo Li Jeon et al., Nature Biotechnology, vol. 20, Jul. 2002, pp. 826-830.

* cited by examiner

*Primary Examiner* — Sath V. Perungavoor
*Assistant Examiner* — Jason Heidemann
(74) *Attorney, Agent, or Firm* — Boyle Fredrickson, S.C.

(57) ABSTRACT

A method of quantifying cell migration of a cell population is provided. The method includes the step of patterning the cell population within a channel network in a first body. A first image of the cell population is obtained. Thereafter, a second image of the cell population is obtained after a first predetermined time period. The first and second images are compared in order to calculate a quantitative measure of the average directional migration of the cells population and a quantitative measure of the average motility of the cell population.

25 Claims, 4 Drawing Sheets

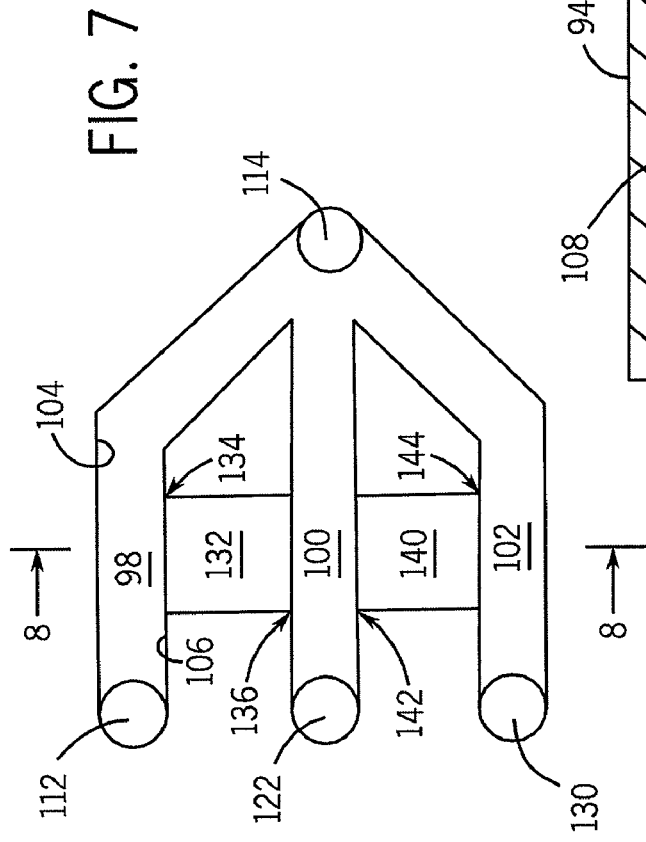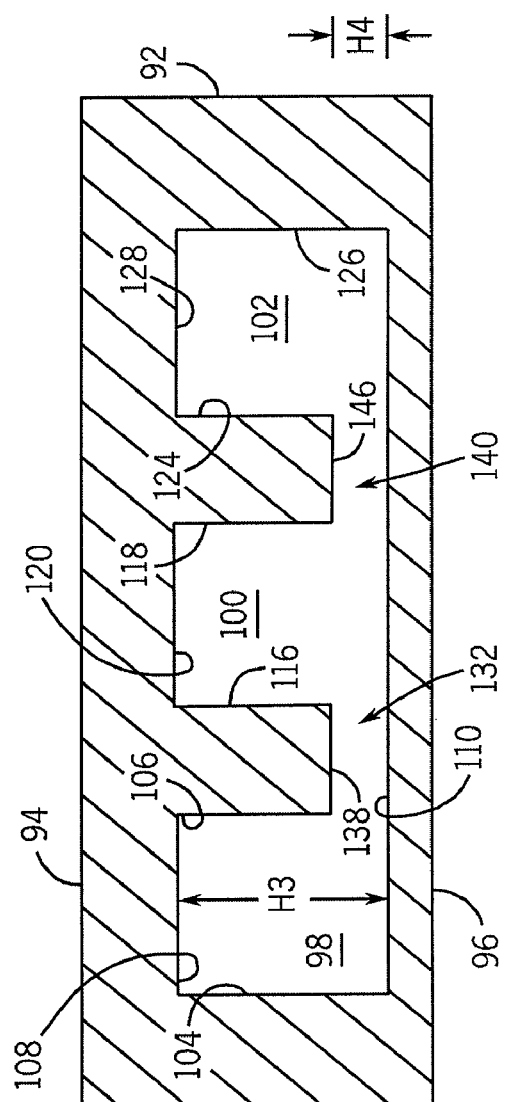

METHOD FOR QUANTIFYING CELL MOTILITY AND CELL MIGRATION

REFERENCE TO GOVERNMENT GRANT

This invention was made with United States government support awarded by the following agencies: ARMY/MRMC W81XWH-04-1-0572 and NIH CA104162. The United States has certain rights in this invention.

FIELD OF THE INVENTION

This invention relates generally to cell migration, and in particular, to a method for quantifying cell motility and cell migration.

BACKGROUND AND SUMMARY OF THE INVENTION

Migration is a cellular process important for many physiological functions. During development, cells rearrange to form structured tissues and organs, and in the adult, leukocytes exit the blood stream and move into tissue in response to signals reporting the presence of foreign invaders. In cancer, metastases are formed by migrating cancer cells. In the first two examples above, migration is directional toward a specific target. This behavior is known a chemotaxis and is brought about by a gradient of chemoattractants or chemokines that migrating cells are able to sense and orient their polarization (i.e. axis of migration) accordingly. Some cells migrate randomly in the absence of chemokine gradients. Cytokines may cause those cells to migrate at a faster pace, although still randomly, a process known as cytokinesis.

Many different methods have been developed to study cell migration. Choosing between those methods generally involves a trade-off between throughput and information content. On one end of the spectrum lies the Dunn chamber in which a gradient is formed between a circular chamber and a concentric annular chamber etched in glass. A coverslip with cells growing on it is then inverted on top of the chambers and their migration in the vicinity of the annular bridge between the chambers is recorded using video-microscopy. Later (i.e. off-line) individual cells are identified manually (sometimes semi-automatically) and their position tracked over time. The Dunn chamber is very low throughput but yields precise information about individual cell behavior. Such detail is important for studies of the fundamental mechanisms of cell migration but may not be practical for studying the effect of numerous conditions, such as in anti-inflammatory drug screening. On the opposite end of the spectrum we have microtiter plate-insert transwell assays, wherein cells are seeded on a porous membrane suspended in a microtiterplate and a chemoattractant is introduced on the opposite side of the membrane. The chemoattractant diffuses through the membrane forming a gradient. A typical readout entails removal of the cells on the side where they were seeded and quantification of the cell number on the other side. As an example, cells can be manually scraped from the original side so that the transwell insert only contains cells that have traversed the membrane. Alternatively, only cells that fall from the membrane to the bottom of the well below may be included in the readout. The cells may be quantified by cell lysis and an Adenosine Triphosphate (ATP) measurement via bioluminescence which can be detected using a plate reader. In the case of transwell assays, the steepness of the gradient is hard to determine, and no distinction is made between chemokinesis, chemotaxis, or even cell death. Additionally, the inserts themselves are expensive and the specific steps of the assay, namely, the removal of non-migrating cells and the washing of cells on the underside of the membrane, are non-trivial to automate.

As is known, microtechnology has been applied to make precise soluble gradients with a variety of spatial and temporal profiles, as well as, surface-bound gradients. Microfluidic gradient generation devices have been employed to study the migration of blood cells, cancer cells, neurons, as well as, bacteria. However, assays that seed cells randomly in a chamber and employ laminar flow to create a gradient rely on video-microscopy for readout, and thus, limits throughput and requires expensive software for data analysis. Additionally, the presence of flow may eliminate potential paracrine signals that are involved in the biological process of interest. For example, if a drug is to be developed that affects tissue resident cells that produce the stimulus for white blood cell migration into tissue, the presence of flow in the screening assay would abolish this signal and lead to the discovery of drugs that treat the symptom rather than the root of the problem.

Therefore, it is a primary object and feature of the present invention to provide a method for quantifying cell motility and cell migration.

It is a further object and feature of the present invention to provide a method for studying cell migration that allows a user to simply and easily determine the quantitative motility and directional migration data for a cell population.

It is a still further object and feature of the present invention to provide a method for studying cell migration that combines microfluidic gradient generation with micro-patterning to simplify the extraction of important migratory information.

In accordance with the present invention, a method of quantifying cell migration of a cell population is provided. The method includes the steps of patterning the cell population within a channel network through a first body and obtaining an first image of the cell population. A second image of the cell population is obtained after a first predetermined time period. Thereafter, the first and second images are compared.

The channel is defined by a first sidewall and the method contemplates the additional step of providing a first predetermined medium along the first sidewall. In addition, may be defined by a second sidewall. A second predetermined medium may be provided along the second sidewall. Alternatively, a predetermined medium may be provided in a second channel through the first body. The second channel is interconnected to the first channel. The first channel may include an input and an output, and the second channel includes an input and an output communicating with the output of the first channel.

The channel network is defined by a first sidewall and the method may include the additional step of providing a first predetermined medium along the first sidewall. In addition, the channel network may be defined by a second sidewall and the method may include the additional step of providing a second predetermined medium along the second sidewall.

The channel network may include first and second interconnected channels. A predetermined medium may be provided in the first and second channels. The first channel includes an input and an output and the second channel includes an input and an output communicating with the output of the first channel. The first and second channels communicate along a cross channel. The first channel has a first cross-sectional area and the second channel has a second cross-sectional area. The cross channel has a cross-sectional area smaller than the cross-sectional areas of the first and second channels.

The method may include the additional steps of patterning a second cell population within a channel network through a second body and obtaining an image of the second cell population after the first predetermined time period. The image of the second cell population is compared with the second image of the first cell population.

The step of comparing may includes the additional steps of calculating a first center of gravity for the cell population at a first initial time and calculating a second center of gravity for the cell population after the predetermined time period. The absolute difference between the first and second centers of gravity is a quantitative measure of the average directional migration of the cells population. In addition, a first full-width at half mass for the cell population is calculated at a first initial time and at after a predetermined time period. The absolute difference between the first full-width at half mass and the second full-width at half mass is a quantitative measure of the average motility of the cell population. Other comparable measures can be envisioned, such as the parameters acquired via curve-fitting of the cell distribution using known distribution functions such as the Gaussian distribution. In the case of the Gaussian distribution the center of mass and full width at half mass would be replaced by the mean (position) and the variance respectively.

In accordance with a further aspect of the present invention, a method of quantifying cell migration of a cell population is provided. The method includes the step of patterning the cell population within a channel network in a first body. The cell population is observed at a first predetermined time period and at a second predetermined time period.

The method includes the additional of step of providing a first predetermined medium in communication with the channel network. The channel network is defined by first and second sidewalls. The step of providing a first predetermined medium in communication with the channel network includes the additional step of patterning the predetermined medium along at least one of the first and second sidewalls.

The channel network includes first and second interconnected channels. The first and second channels are interconnected by a cross-channel. The first channel has a first cross-sectional area and the second channel has a second cross-sectional area. The cross channel has a cross-sectional area smaller than the cross-sectional areas of the first and second channels.

The step of observing the cell population at a second predetermined time period includes the steps of calculating a quantitative measure of the average directional migration of the cells population and calculating a quantitative measure of the average motility of the cell population. This is accomplished by calculating a first center of gravity for the cell population at a first initial time and calculating a second center of gravity for the cell population after the predetermined time period. The absolute difference between the first and second centers of gravity is a quantitative measure of the average directional migration of the cells population. In addition, a first full-width at half mass for the cell population is calculated at a first initial time and after the predetermined time period. The absolute difference between the first full-width at half mass and the second full-width at half mass is a quantitative measure of the average motility of the cell population.

In accordance with a still further aspect of the present invention, a method is provided for quantifying cell migration of a cell population. The method includes the step of patterning the cell population within a channel network through a first body. A predetermined medium in communication with the first channel is provided. Thereafter, migration of the cell population is observed over a predetermined time period.

The channel network is defined by first and second sidewalls and the step of providing the predetermined medium in communication with the channel network includes the additional step of patterning the predetermined medium along the first and second sidewalls. The channel network may include first and second channels. The first and second channels are interconnected by a cross-channel. The first channel has a first cross-sectional area and the second channel has a second cross-sectional area. The cross channel has a cross-sectional area smaller than the cross-sectional areas of the first and second channels.

The step of observing the cell population at a second predetermined time period includes the steps of calculating a quantitative measure of the average directional migration of the cells population and calculating a quantitative measure of the average motility of the cell population. This is accomplished by calculating a first center of gravity for the cell population at a first initial time and calculating a second center of gravity for the cell population after the predetermined time period. The absolute difference between the first and second center of gravities is a quantitative measure of the average directional migration of the cells population. In addition, a first full-width at half mass for the cell population is calculated at a first initial time and after the predetermined time period. The absolute difference between the first full-width at half mass and the second full-width at half mass is a quantitative measure of the average motility of the cell population.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 7 is a schematic view of a further alternate embodiment of a device for effectuating the methodology of present invention;

FIG. 8 is a cross-sectional view of the alternate embodiment of the device of the present invention, taken along line 8-8 of FIG. 7.

DETAILED DESCRIPTION OF THE DRAWINGS

Figure 1:
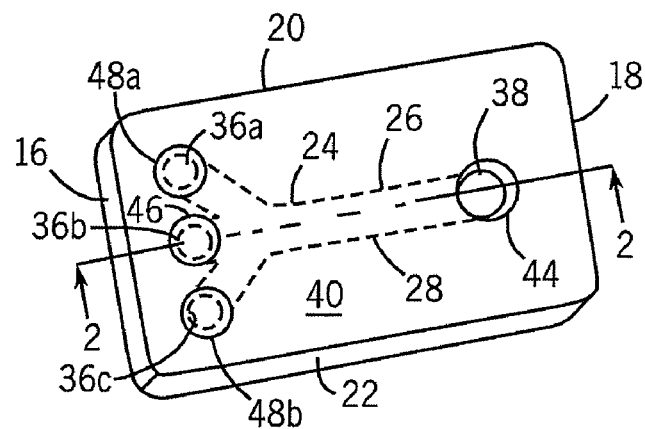
FIG. 1 is an isometric view of an exemplary device for effectuating a methodology in accordance with the present invention.
Figure 2:
FIG. 2 is a cross-sectional view of the device taken along line 2-2 of FIG. 1.

Referring to FIGS. 1-4b, an exemplary device for effectuating the methodology of the present invention is generally designated by the reference numeral 10. Device 10 includes first and second ends 16 and 18, respectively, and first and second sides 20 and 22, respectively. Channel 24 extends through device 10 along a longitudinal axis and is defined by first and second spaced sidewalls 26 and 28, respectively, and upper and lower walls 30 and 31, FIG. 2. Channel 24 further includes first and second ends 32 and 34, respectively, that communicate with a plurality of inlets 36a-36c and outlet 38, respectively. Inlets 36a-36c and outlet 38 communicate with upper surface 40 of device 10.

It is contemplated for outlet 38 of channel 24 to have a generally cylindrical shape to allow for robust and easy access via droplet touch off using a micropipette of a robotic micropipetting station. Surface tension will lead to pumping from smaller drops to a larger drop. It is further contemplated for the portions of upper surface 40 about inlets 36a-36c and for inner surface 41 defining each inlet 36a-36c to be physically, chemically or structurally patterned to contain fluid drops therein and prevent cross channel contamination with the other inlets of channel 24. Similarly, each inlet 36a-36d of channel 24 may have a generally cylindrical shape to allow for robust and easy access via droplet touch off using a micropipette. In addition, a portion of upper surface 40 of device 10 about outlet 38 or inner surface 43 defining outlet 38 may be physically or structurally patterned to contain fluid droplets within/adjacent outlet 38.

In a first embodiment, a suspension is prepared containing cells 42 of interest. Channel 24 is filled with a culture medium and large drop 44, FIG. 2, of the culture medium is deposited on outlet 38. The suspension containing cells 42 are introduced at inlet 36b via drops 46. Simultaneously, drops 48a and 48b of a desired media are provided at inlets 36a and 36c. As is known, because drops 46 and 48a-48b have a smaller radius than drop 44 at outlet 38, a larger pressure exists on inlets 36a-36c of channel 24. The resulting pressure gradient causes drops 48a, 46 and 48b to flow from corresponding inlets 36a-36c through channel 24 towards drop 44 over outlet 38 of channel 24. It can be understood that by simultaneously depositing additional drops 48a, 46 and 48b on corresponding inlets 36a-36c of channel 24 by a micropipette of a robotic micropipetting station, the resulting pressure gradient will cause laminar flow of drops 48a, 46 and 48b through channel 24 towards drop 44 over outlet 38 of channel 24. After a predetermined time period, cells 42 are patterned within channel 24 such that cells 42 are uniformly dispersed along the central axis of the channel and uniformly dispersed along the y-axis in the form of a generally rectangular strip, generally designated by the reference numeral 50. Thereafter, the flow though channel 24 is stopped.

In the cell migration quantification method of the present invention, the density of cells 42 in channel 24 along the x-axis is monitored and quantified by calculating two parameters, the center of gravity and the full width at half mass, as hereinafter described. More specifically, the absolute difference of the center of gravity between first and second time periods provides a quantitative measure of the average directional migration of cells 42. The absolute difference of the full-width at half mass between first and second time periods provides a quantitative measure of the average motility of cells 42.

Figure 3A:
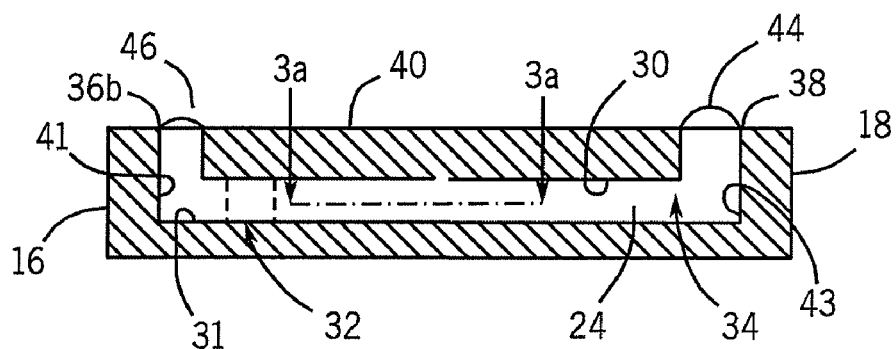
FIG. 3a is a cross-sectional view of the device taken along line 3a-3a of FIG. 2 showing an initial state of a plurality of cells patterned within a channel of the device.
Figure 3A:
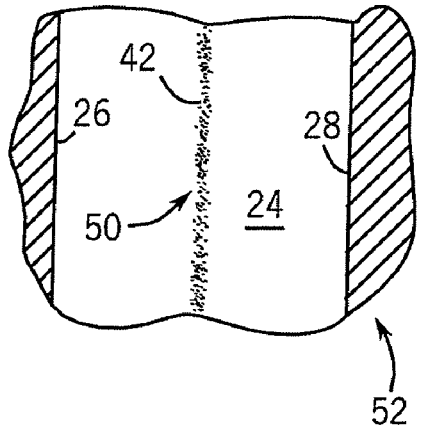

Once cells 42 are patterned in channel 24, first image 52 is taken to capture the initial positions of cells 42, FIG. 3a. After a first predetermined time period, second image 54 is taken to capture the intermediate positions of cells 42, FIG. 3b. Finally, after a second predetermined time period, third image 56 is taken to capture the final positions of cells 42, FIG. 3c. Once images 52, 54 and 56 have been obtained, each image 52, 54 and 56 can be treated as a two-dimensional N-by-M matrix, J, wherein the positions of cells 42 are digitally represented by finite areas of non-zero elements, and that the areas surrounding cells 42 are represented are digitally represented by zero elements in the matrix. As such, it can be appreciated that the distribution of cells 42 in image 52 can be determined. It is assumed that the integrated intensities of the areas that represent single cells 42 are randomly distributed across the population. The process is repeated to determine the positions of cells 42 in the second and third images 54 and 56, respectively.

In order to determine the quantitative measures of the directional migration and motility of cells 42, the center of gravity of the distribution of cells 42 and the full-width half mass of the cells 42 are calculated for each image 52, 54, and 56. Cell distribution along the x-axis of channel 24 is given by the equation:

$$I[n] = \sum_{m=1}^{M} J[n, m] \quad \text{Equation (1)}$$

wherein: I[n] is the cell distribution; n is the number of columns in the matrix; m is the number of rows in the matrix; and J is the matrix.

The total mass of cells 42 in an image, T, is given by the equation:

$$T = \sum_{n=1}^{N} \sum_{m=1}^{M} J[n, m] \quad \text{Equation (2)}$$

wherein: T is the total mass of cells 42 in an image; n is the number of columns in the matrix; m is the number of rows in the matrix; and J is the matrix.

The center of gravity, C, is given by the equation:

$$C = \frac{1}{T} \sum_{n=1}^{N} n I[n] \quad \text{Equation (3)}$$

wherein: C is the center of gravity; T is the total mass of cells 42 in an image; n is the number of columns in the matrix; m is the number of rows in the matrix; and I[n] is the cell distribution.

The full-width at half mass, W, is given by the equation $$W = 2s + 1 \quad \text{Equation (4)}$$

wherein: W is the full-width at half mass; and s is the smallest number that satisfies the following equation:

$$\sum_{n=C-s}^{C+s} \geq \frac{1}{2} T \qquad \text{Equation (5)}$$

The value of s is determined by iterative addition of elements starting from the center of gravity, C, according to the following steps:
s=1
while m<0.5×T
    m=m+I(C−s)+I(C+s)
    s=s+1
end
wherein: m is a temporary variable denoting the total mass of the cells located between (C−s) and (C+s) after each step. Once the condition of m≧0.5T is satisfied, the full-width at half mass, W, can be found using Equation (4).

Figure 3B:
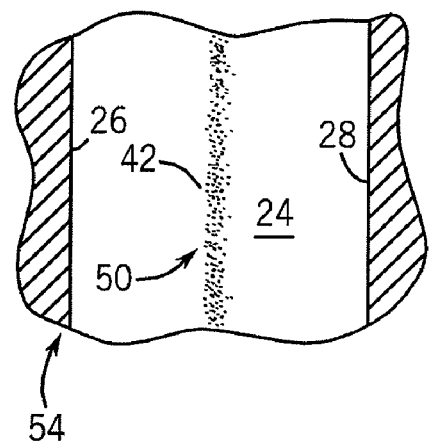
FIG. 3b is a cross-sectional view of the device, similar to FIG. 3a, showing the plurality of cells within the channel of the device after a first predetermined time period.
Figure 3C:
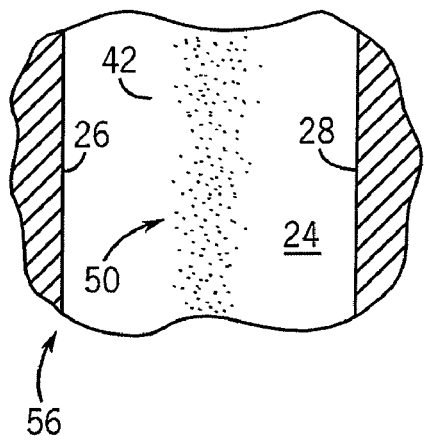
FIG. 3c is a cross-sectional view of the device, similar to FIG. 3a, showing the plurality of cells within the channel of the device after a second predetermined time period.

Once the center of gravity of the distribution of cells 42 and the full-width half mass of the cells 42 are calculated for each image 52, 54, and 56, the calculated center of gravity values for images 54 and 56 are compared with the center of gravity value for the initial image 52. The absolute difference between the center of gravity of each image 52, 54 and 56 are a quantitative measure of the average directional migration of cells 42. For example, it can be appreciated that in cells 42 in FIGS. 3a-3c have no directional preference. In addition, the full-width half masses for images 54 and 56 are compared with the full-width half mass for the initial image 52. The absolute difference between the full-width half mass values of each image 52, 54 and 56 are a quantitative measure of the average motility of cells 42. For example, it can be appreciated that cells 42 in FIGS. 3a-3c are motile, such that the width of their distribution is increased between the first and second predetermined time points.

Figure 4A:
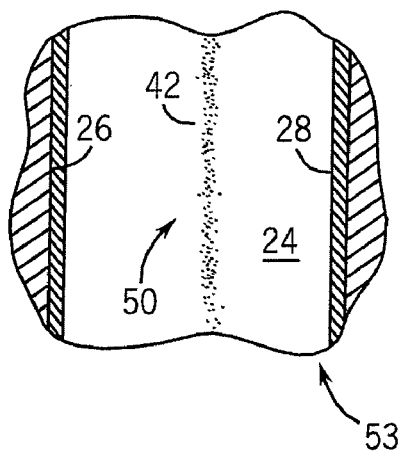
FIG. 4a is a cross-sectional view of the device, similar to FIG. 3b, showing the plurality of cells within an alternate channel of the device after a first predetermined time period.
Figure 4B:
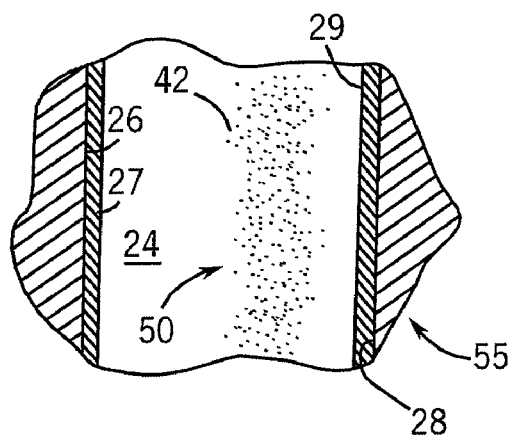
FIG. 4b is a cross-sectional view of the device, similar to FIG. 3c, showing the plurality of cells within an alternate channel of the device after a second predetermined time period.

Alternatively, referring FIGS. 4a-4b, it is contemplated to introduce a suspension containing cells 42 at inlet 36b via drops 46. Simultaneously, drops 48a and 48b of culture medium are provided at inlets 36a and 36c. As is known, because drops 46 and 48a-48b have a smaller radius than drop 44 at outlet 38, a larger pressure gradient exists on inlets 36a-36c of channel 24. The resulting pressure gradient causes the laminar flow of drops 48a, 46 and 48b from corresponding inlets 36a-36c through channel 24 towards drop 44 over outlet 38 of channel 24. It can be understood that by sequentially depositing additional drops 48a, 46 and 48b on corresponding inlets 36a-36c of channel 24 by a micropipette of robotic micropipetting station, the resulting pressure gradient will cause the drops 48a, 46 and 48b deposited on corresponding inlets 36a-36c to flow through channel 24 towards drop 44 over outlet 38 of channel 24. It can be appreciated that after a predetermined time period, cells 42 are patterned within channel 24 such that cells 42 are uniformly dispersed along the central axis of the channel and uniformly dispersed along the y-axis in the form of a generally rectangular strip, generally designated by the reference numeral 50. Thereafter, the flow though channel 24 is stopped. It is further contemplated to pattern first and second media 27 and 29, respectively, e.g. a chemoattractant, along sidewalls 26 and 28 of channel 24 on opposite sides of cells 42. It can be appreciated that using the method of the present invention heretofore described, various media may be tested in order to determine a media's ability to promote or discourage the motility or migration of cells 42.

Once cells 42 are patterned in channel 24, first image 53 is taken to capture the initial positions of cells 42, FIG. 4a. After a first predetermined time period, second image 55 is taken to capture the positions of cells 42, FIG. 4b. Once images 53 and 55 have been obtained, each image 53 and 55 can be treated as a two-dimensional N-by-M matrix, J, wherein the positions of cells 42 are digitally represented by finite areas of non-zero elements, and that the areas surrounding cells 42 are represented are digitally represented by zero elements in the matrix. As such, it can be appreciated that the positions of cells 42 in image 53 can be determined. It is assumed that the integrated intensities of the areas that represent single cells 42 are randomly distributed across the population. The process is repeated to determine the positions of cells 42 in the second image 55.

As heretofore described, in order to determine the quantitative measures of the directional migration and motility of cells 42, the center of gravity of the distribution of cells 42 and the full-width half mass of the cells 42 are calculated for each image 53 and 55. The absolute difference between the center of gravity for images 53 and 55 is a quantitative measure of the average directional migration of cells 42. For example, it can be appreciated that in cells 42 in FIGS. 4a-4b have a directional preference towards medium 29. In addition, the full-width half masses for images 53 and 55 are compared. The absolute difference between the full-width half mass values of image 53 and 55 is a quantitative measure of the average motility of cells 42.

Figure 5:
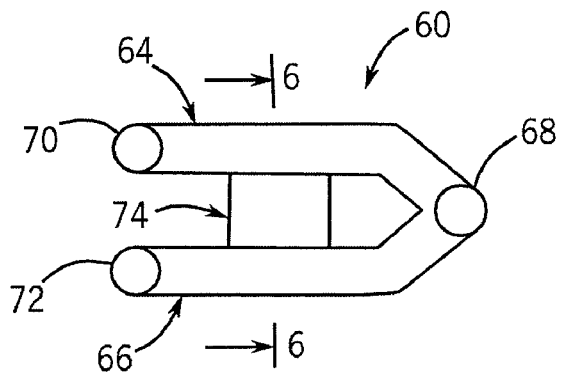
FIG. 5 is a schematic view of an alternate embodiment of a device for effectuating the methodology of present invention.
Figure 6:
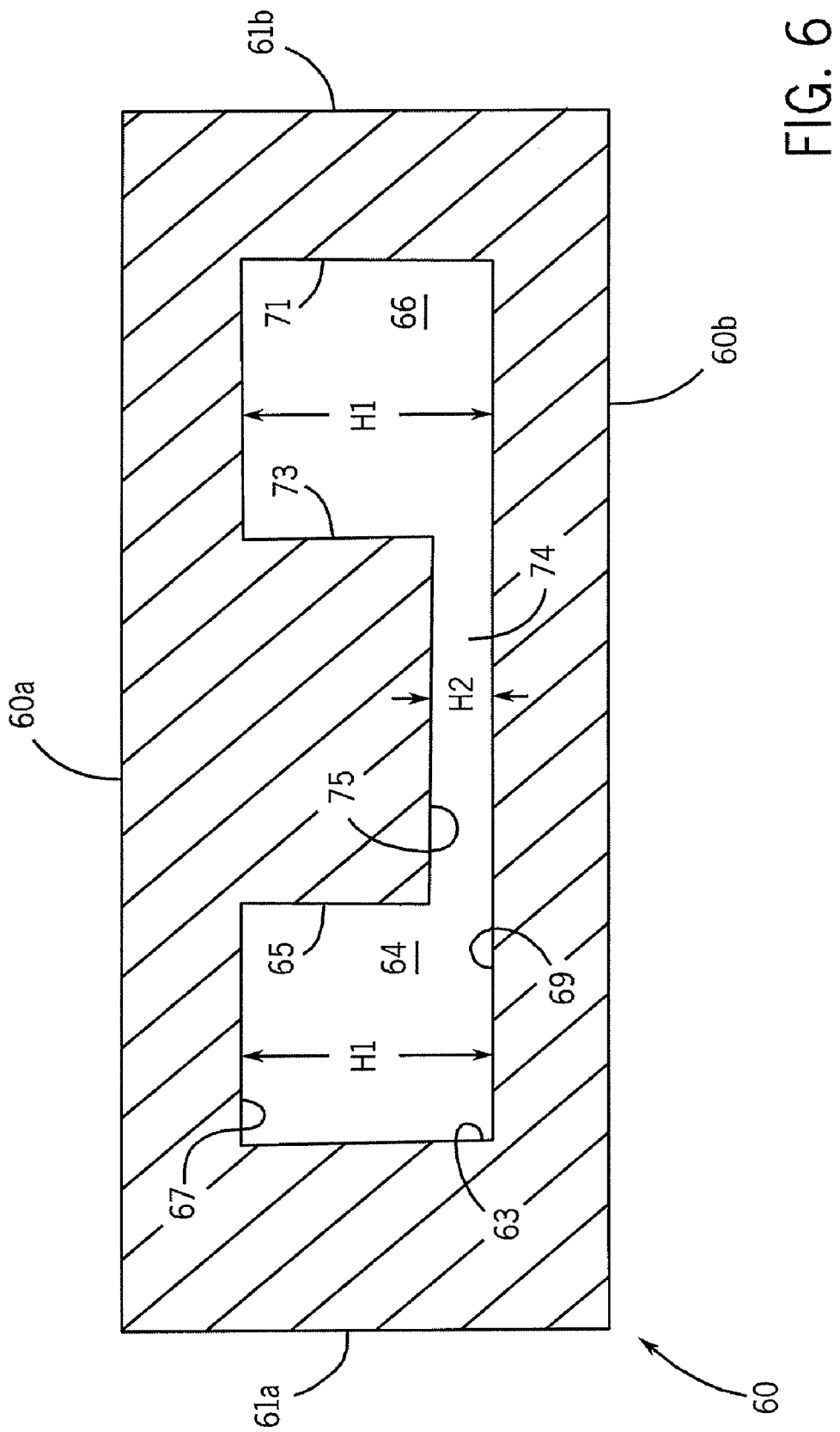
FIG. 6 is a cross-sectional view of the alternate embodiment of the device of the present invention, taken along line 6-6 of FIG. 5.

Referring to FIGS. 5-6, an alternated embodiment of a device for effectuating the methodology of the present invention is generally designated by the reference numeral 60. It is intended for device 60 to provide a user with information regarding the motility and rate of migration of cells. More specifically, device 60 includes upper and lower surfaces 60a and 60b, respectively, and first and second sides 61a and 61b, respectively. Channel 64 extends through device 60 along a longitudinal axis and is defined by first and second spaced sidewalls 63 and 65, respectively, and upper and lower walls 67 and 69, respectively. Channel 66 extends through device 60 along a longitudinal axis and is defined by first and second spaced sidewalls 71 and 73, respectively, and upper and lower walls 75 and 69, respectively. Channels 64 and 66 have a common height H1 and a common outlet 68. In addition, channels 64 and 66 include corresponding inlets 70 and 72, respectively, that communicate with upper surface 60a of device 60.

It is contemplated for outlet 68 of channels 64 and 66 to have a generally cylindrical shape to allow for robust and easy access via droplet touch off from a micropipette of a robotic micropipetting station. It is further contemplated for the portions of upper surface 60a about inlets 70 and 72 and for the inner surfaces defining each inlet 70 and 72 to be physically or structurally patterned to contain fluid drops therein and prevent cross channel contamination with the other inlets of device 60. Similarly, each inlet 70 and 72 of channels 64 and 66 may have a generally funnel-shaped cross section to allow for robust and easy mating with the micropipette. In addition, a portion of upper surface 60a of device 60 about outlet 68 and/or the inner surface defining outlet 68 may be physically or structurally patterned to contain fluid drops within/adjacent outlet 68.

Channels 64 and 66 are interconnected by cross channel 74 having a first end 76 communicating with first channel 64 and a second end 78 communicating with second channel 68. Cross channel 74 is partially defined by upper wall 75 and lower wall 69. Cross channel 74 has height H2 that is significantly less than the height H1 of first and second channels 66 and 68, respectively, for reasons hereinafter described. By way of example, height H1 of channels 66 and 68 may be ten (10) times greater than height H2 of cross channel 74. It can be appreciated that given its smaller height H1, cross channel 74 has a higher fluidic resistance than channels 64 and 66.

In operation, channels 64, 66 and 74 are filled with a culture medium and a large drop of the culture medium is deposited on outlet 68. A suspension containing cells 42 is introduced at inlets 70 and 72 via drops. The drops deposited on inlets 70 and 72 have a smaller radius of curvature than the drop at outlet 68. As a result, a larger pressure gradient exists on inlets 70 and 72 of channels 64 and 66. The resulting pressure gradient causes the flow of the drops introduced at inlets 70 and 72 towards the drop over outlet 68 of channels 64 and 66. It can be understood that by sequentially depositing additional drops on corresponding inlets 70 and 72 of channels 64 and 66 by a micropipette of robotic micropipetting station, the resulting pressure gradient will cause the drops introduced at inlets 70 and 72 to flow through channels 64 and 66 towards the drop over outlet 68 of channels 64 and 66. However, given the high fluid resistance of cross channel 78, the suspension is discouraged from flowing into cross channel 78. It can be appreciated that after a predetermined time period, cells 42 are patterned and uniformly dispersed along the channels 64 and 66, but not cross channel 78. Thereafter, the flow of the suspension though channels 64 and 66 is stopped.

Once cells 42 are patterned within channels 64 and 66, a user selected medium is introduced at inlets 70 and 72 via drops. The drops of medium deposited on inlets 70 and 72 have a smaller radius of curvature than the drop at outlet 68. As a result, a larger pressure gradient exists on inlets 70 and 72 of channels 64 and 66. The resulting pressure gradient causes the flow of the drops of the medium introduced at inlets 70 and 72 towards the drop over outlet 68 of channels 64 and 66. It can be understood that by sequentially depositing additional drops on corresponding inlets 70 and 72 of channels 64 and 66 by a micropipette of a robotic micropipetting station, the resulting pressure gradient will cause the drops of medium introduced at inlets 70 and 72 to flow through channels 64 and 66 towards the drop over outlet 68 of channels 64 and 66. It can be appreciated that after a predetermined time period, cells 42 patterned within channels 64 and 66 are exposed to the medium along the entire length of channels 64 and 66. Thereafter, the flow though channels 64 and 66 is stopped.

Once the flow of the medium though channels 64 and 66 is stopped, a first image of cross channel 78 is taken to capture the initial positions of cells 42 in cross channel 78. After a first predetermined time period, a second image is taken to capture the positions of cells 42 in cross channel 78. Once the first and second images have been obtained, the two images are compared to each other. It can be appreciated that one can quantify the migration of cells 42 in response to the medium introduced into channels 64 and 66. In addition, each image can be treated as a two-dimensional N-by-M matrix, J, as heretofore described. By calculating the full-width half mass values of the cell populations in the images, a quantitative measure of the average motility of cells 42 in response to the medium may be determined.

Referring to FIGS. 7-8, a still further embodiment of a device for effectuating the methodology of the present invention is generally designated by the reference numeral 80. Device 80 includes first and second ends (not shown), first and second sides 90 and 92, respectively, and upper and lower surfaces 94 and 96, respectively. Device 90 further includes first, second and third channels 98, 100 and 102, respectively, therein. First channel 98 extends through device 90 along a longitudinal axis and is defined by first and second spaced sidewalls 104 and 106, respectively, and upper and lower walls 108 and 110, respectively. A first end of first channel 98 communicates with inlet 112 and a second end of first channel 98 communicates with outlet 114. Second channel 100 extends through device 90 along a longitudinal axis and is defined by first and second spaced sidewalls 116 and 118, respectively, and upper and lower walls 120 and 110, respectively. A first end of second channel 100 communicates with inlet 122 and a second end of second channel 100 communicates with outlet 114. Third channel 102 extends through device 90 along a longitudinal axis and is defined by first and second spaced sidewalls 124 and 126, respectively, and upper and lower walls 128 and 110, respectively. A first end of third channel 102 communicates with inlet 130 and a second end of third channel 102 communicates with outlet 114. First, second and third channels 98, 100 and 102 have a common height H1 and common outlet 114. Common outlet 114, as well as, inlets 112, 122 and 130 of corresponding channels 98, 100 and 102, respectively, communicate with upper surface 94 of device 90.

It is contemplated for outlet 114 of first, second and third channels 98, 100 and 102, respectively, to have a generally cylindrical shape to allow for robust and easy access via droplet touch off from a micropipette of a robotic micropipetting station. It is further contemplated for the portions of upper surface 94 about inlets 112, 122 and 130 and for the inner surfaces defining inlets 112, 122 and 130 to be physically, chemically or structurally patterned to contain fluid drops therein and prevent cross channel contamination with the other inlets of device 90. Similarly, inlets 112, 122 and 130 of first, second and third channels 98, 100 and 102, respectively, may have a generally funnel-shaped cross section to allow for robust and easy mating with the micropipette. In addition, a portion of upper surface 94 of device 90 about outlet 114 and/or the inner surface defining outlet 114 may be physically, chemically or structurally patterned to contain fluid drops within/adjacent outlet 114.

First and second channels 98 and 100, respectively, are interconnected by cross channel 132 having first end 134 communicating with first channel 98 and second end 136 communicating with second channel 100. Cross channel 132 is defined by upper wall 138 and lower wall 110. Second and third channels 98 and 100, respectively, are interconnected by cross channel 140 having a first end 142 communicating with second channel 100 and a second end 144 communicating with third channel 102. Cross channel 140 is partially defined by upper wall 146 and lower wall 110. Cross channels 132 and 140 have a common height H2 that is significantly less than the height H1 of first, second and third channels 98, 100 and 102, respectively, for reasons hereinafter described. By way of example, height H1 of first, second and third channels 98, 100 and 102, respectively, may be approximately ten (10) times greater than height H2 of cross channels 132 and 140. It can be appreciated that given their smaller height H1, cross channels 132 and 140 have higher fluidic resistances than first, second and third channels 98, 100 and 102, respectively.

In operation, cross channels 132 and 140 and first, second and third channels 98, 100 and 102, respectively, are filled with a culture medium and a large drop of the culture medium is deposited on outlet 114. A suspension containing cells is introduced at inlet 122 of second channel 100 via a drop. The drop deposited on inlet 122 has a smaller radius of curvature than the drop at outlet 114. As a result, a large pressure gradient exists on inlet 122 of second channel 100. The resulting pressure gradient causes the drop introduced at inlet 122 to flow towards the drop over outlet 114 of second channel 100. Drops of media are introduced at inlets 112 and 130 of first and third channels 98 and 102, respectively. It is contemplated for one of the media introduced at inlets 112 and 130 of first and third channels 98 and 102, respectively, to contain a chemoattractant. It can be understood that by sequentially depositing additional drops on corresponding inlets 112, 122 and 130 of first, second and third channels 98, 100 and 102, respectively, by a micropipette of robotic micropipetting station, the resulting pressure gradient will cause the drops introduced at inlets 112, 122 and 130 of first, second and third channels 98, 100 and 102, respectively, to flow through first, second and third channels 98, 100 and 102, respectively, towards the drop over outlet 114 of first, second and third channels 98, 100 and 102. However, given the high fluid resistance of cross channels 132 and 140, the suspension in second channel 100 and the media in first and third channels 98 and 102, respectively, is discouraged from flowing into cross channels 132 and 140. Hence, it can be appreciated that after a predetermined time period, the cells in the suspension are patterned and uniformly dispersed along second channel 100, but not cross channels 132 and 140. Thereafter, the flow of the suspension though first, second and third channels 98, 100 and 102, respectively, is stopped.

Once the flow of the media though first, second and third channels 98, 100 and 102, respectively, is stopped, a first image of cross channels 132 and 140 is taken to capture the initial positions of the cells in cross channels 132 and 140. After a first predetermined time period, a second image is taken to capture the positions of the cells in cross channels 132 and 140. Once the first and second images have been obtained, the two images are compared to each other. It can be appreciated that one can quantify the migration of the cells in response to the media introduced into first and third channels 98 and 102, respectively. In addition, each image can be treated as a two-dimensional N-by-M matrix, J, as heretofore described. By calculating the full-width half mass values of the cell populations in the images, a quantitative measure of the average motility of the cells in response to the media may be determined.

It can be appreciated that the method of the present invention presents a novel method to quantify cell motility and migration. The method does not involve the tracking of individual cells, but rather extraction of cell population parameters for the cell population as a whole. Through simple computations, the method directly provides quantitative motility and directional migration data for a population and is sensitive to small effects due to inherent averaging across the population. The simplicity of the method renders it easy to use and amenable to high throughput operation.

Various modes of carrying out the invention are contemplated as being within the scope of the following claims particularly pointing out and distinctly claiming the subject matter, which is regarded as the invention.

We claim:

1. A method of quantifying cell migration of a cell population, comprising the steps of:
    patterning the cell population within a channel network in a body, the channel network including first and second channels having an outlet and being interconnected by a cross-channel upstream of the outlet;
    providing a first predetermined medium in the first channel;
    providing a second predetermined medium in the second channel; and
    observing migration of the cell population in the cross-channel over time.

2. The method of claim 1 comprising the additional steps of:
    calculating a quantitative measure of the average directional migration of the cell population; and
    calculating a quantitative measure of the average motility of the cell population.

3. The method of claim 1 comprising the additional steps of:
    calculating a first center of gravity for the cell population at a first initial time; and
    calculating a second center of gravity for the cell population after the predetermined time period;
    wherein the absolute difference between the first and second center of gravities is a quantitative measure of the average directional migration of the cell population.

4. A method of quantifying cell migration of a cell population, comprising the steps of:
    patterning the cell population within a channel network in a first body;
    observing the cell population at a first predetermined time period; and
    observing the cell population at a second predetermined time period;
    wherein:
    the channel network includes first, second and third channels;
    the first and second channels are interconnected by a cross-channel;
    the first channel has a first cross-sectional area;
    the second channel has a second cross-sectional area;
    the cross channel has a cross-sectional area smaller than the cross-sectional areas of the first and second channels;
    the second and third channels are interconnected by a second cross-channel;
    the third channel has a third cross-sectional area; and
    the second cross channel has a cross-sectional area smaller than the cross-sectional areas of at least one of the first, second and third channels.

5. A method of quantifying cell migration of a cell population, comprising the steps of:
    patterning the cell population within a channel network in a first body;
    obtaining an first image of the cell population;
    obtaining a second image of the cell population after a first predetermined time period;
    comparing the first and second images, the first and second images compared by:
        calculating a first full-width at half mass for the cell population at a first initial time; and
        calculating a second full-width at half mass for the cell population after the first predetermined time period;
    wherein the absolute difference between the first full-width at half mass and the second full-width at half mass is a quantitative measure of the average motility of the cell population.

6. The method of claim 5 wherein the channel network is defined by a first sidewall and wherein the method further comprises the additional step of providing a first predetermined medium along the first sidewall.

7. The method of claim 6 wherein the channel network is defined by a second sidewall and wherein the method further comprises the additional step of providing a second predetermined medium along the second sidewall.

8. The method of claim 5 wherein the channel network includes first and second channels and wherein the method further comprises the additional steps:
    interconnecting the first and second channels; and
    providing a predetermined medium in the first and second channels.

9. The method of claim 8 wherein:
    the first channel includes an input and an output; and the second channel includes an input and an output communicating with the output of the first channel.

10. The method of claim 8 wherein the first and second channels communicate along a cross channel.

11. The method of claim 10 wherein:
the first channel has a first cross-sectional area;
the second channel has a second cross-sectional area; and
the cross channel has a cross-sectional area smaller than the cross-sectional areas of the first and second channels.

12. The method of claim 8 comprising the additional steps:
patterning a first cell population within a channel network through a second body;
obtaining an image of the first cell population within the channel network through the second body after the first predetermined time period; and
comparing the image of the first cell population within the channel network through the second body with the second image of the first cell population within the channel network through the first body.

13. The method of claim 5 wherein the step of comparing, includes the additional steps of:
calculating a first center of gravity for the cell population at a first initial time; and
calculating a second center of gravity for the cell population after the predetermined time period;
wherein the absolute difference between the first and second center of gravities is a quantitative measure of the average directional migration of the cell population.

14. A method of quantifying cell migration of a cell population, comprising the steps of:
patterning the cell population within a channel network in a first body;
observing the cell population at a first predetermined time period;
observing the cell population at a second predetermined time period;
calculating a first full-width at half mass for the cell population at the first predetermined time; and
calculating a second full-width at half mass for the cell population at the second predetermined time period;
wherein the absolute difference between the first full-width at half mass and the second full-width at half mass is a quantitative measure of the average motility of the cell population.

15. The method of claim 14 comprising the additional of step of providing a first predetermined medium in communication with the channel network.

16. The method of claim 15 wherein the channel network is defined by first and second sidewalls and wherein the step of providing a first predetermined medium in communication with the channel network includes the additional step of patterning the predetermined medium along at least one of the first and second sidewalls.

17. The method of claim 15 wherein the channel network includes first and second channels, the first and second channels being interconnected.

18. The method of claim 17 wherein:
the first and second channels are interconnected by a cross-channel;
the first channel has a first cross-sectional area;
the second channel has a second cross-sectional area; and
the cross channel has a cross-sectional area smaller than the cross-sectional areas of the first and second channels.

19. The method of claim 14 wherein the step of observing the cell population at a second predetermined time period includes the steps of:
calculating a quantitative measure of the average directional migration of the cell population; and
calculating a quantitative measure of the average motility of the cell population.

20. The method of claim 14 comprising the additional steps of:
calculating a first center of gravity for the cell population at a first initial time; and
calculating a second center of gravity for the cell population after the predetermined time period;
wherein the absolute difference between the first and second center of gravities is a quantitative measure of the average directional migration of the cell population.

21. A method for quantifying cell migration of a cell population, comprising the steps of:
patterning the cell population within a channel network through a first body;
providing a predetermined medium in communication with the channel network;
observing migration of the cell population over a predetermined time period;
calculating a first full-width at half mass for the cell population at a first initial time; and
calculating a second full-width at half mass for the cell population after the predetermined time period;
wherein the absolute difference between the first full-width at half mass and the second full-width at half mass is a quantitative measure of the average motility of the cell population.

22. The method of claim 21 wherein the channel network is defined by first and second sidewalls and wherein the step of providing the predetermined medium in communication with the channel network includes the additional step of patterning the predetermined medium along the first and second sidewalls.

23. The method of claim 21 wherein:
the channel network includes first and second channels;
the first and second channels are interconnected by a cross-channel;
the first channel has a first cross-sectional area;
the second channel has a second cross-sectional area; and
the cross channel has a cross-sectional area smaller than the cross-sectional areas of the first and second channels.

24. The method of claim 21 wherein the step of observing migration of the cell population includes the steps of:
calculating a quantitative measure of the average directional migration of the cell population; and
calculating a quantitative measure of the average motility of the cell population.

25. The method of claim 21 comprising the additional steps of:
calculating a first center of gravity for the cell population at a first initial time; and
calculating a second center of gravity for the cell population after the predetermined time period;
wherein the absolute difference between the first and second center of gravities is a quantitative measure of the average directional migration of the cell population.

* * * * *